Figure 1:
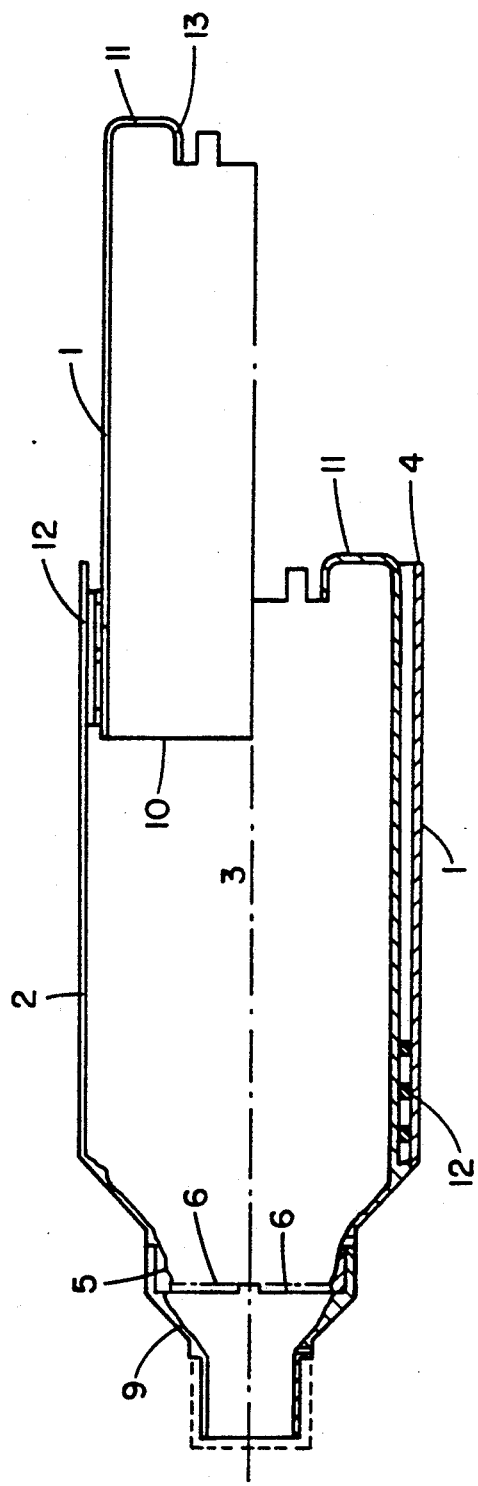
Figure 4:
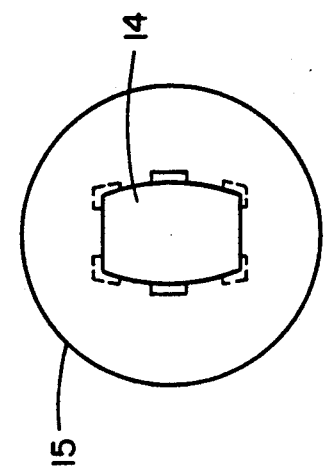
Figure 3:
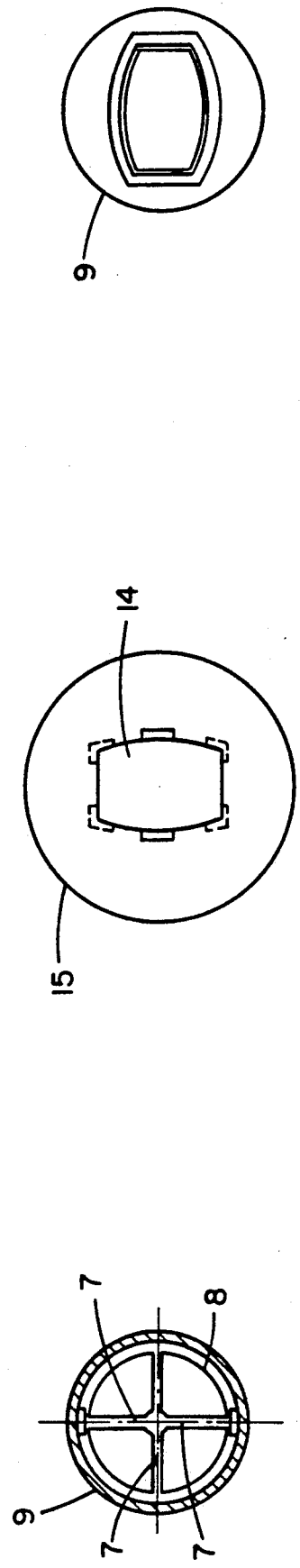
Figure 2:
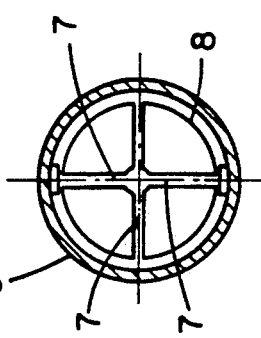

United States Patent [19]

Chiesi

[11] Patent Number: 5,074,294
[45] Date of Patent: Dec. 24, 1991

[54] DEVICE FOR DISPENSING METERED AMOUNTS OF AEROSOL FOR INHALATION

[75] Inventor: Paolo Chiesi, Parma, Italy
[73] Assignee: Chiesi Farmaceutici S.p.A., Parma, Italy
[21] Appl. No.: 369,298
[22] Filed: Jun. 21, 1989

[30] Foreign Application Priority Data

Jun. 22, 1988 [IT] Italy .................... 21065 A/88

[51] Int. Cl.⁵ .................................... A61M 11/00
[52] U.S. Cl. ........................ 128/200.14; 128/200.23
[58] Field of Search ............... 128/200.14, 200.23, 128/203.12, 203.15, 203.21; 222/182

[56] References Cited

U.S. PATENT DOCUMENTS

| | | | |
|---|---|---|---|
| 3,788,316 | 1/1974 | Mora | 128/203.24 |
| 3,809,294 | 5/1974 | Torgeson | 128/203.15 |
| 3,897,779 | 8/1975 | Hansen | 128/203.15 |
| 3,994,421 | 11/1976 | Hansen | 222/182 |
| 4,470,412 | 9/1984 | Nowacki et al. | 128/200.23 |
| 4,534,343 | 8/1985 | Nowacki et al. | 128/203.15 |
| 4,637,528 | 1/1987 | Wachinski et al. | 128/200.23 |
| 4,641,644 | 2/1987 | Anderson et al. | 128/200.23 |
| 4,690,332 | 9/1987 | Hughes | 128/200.18 |

*Primary Examiner*—Edgar S. Burr
*Assistant Examiner*—Aaron J. Lewis
*Attorney, Agent, or Firm*—Bucknam and Archer

[57] ABSTRACT

The invention concerns an apparatus for the administration of drugs in form of metered aerosol, consisting of an expansion chamber comprising two coaxial tubes freely slidable within one another and detachable.

The external tube has an open end and a tapered end on which the chamber month-piece is mounted.

The internal tube has an open end which may be inserted into the external tube and on opposite end on which the month-piece of a conventional dispenser containing the active principle in form of pressurized aerosol is stuck.

The apparatus allows a better penetration of the drug into the airways up to the deepest zones of the bronchial tree.

9 Claims, 1 Drawing Sheet

U.S. Patent      Dec. 24, 1991      5,074,294

DEVICE FOR DISPENSING METERED AMOUNTS OF AEROSOL FOR INHALATION

Inhalation is the preferred way of administering drugs that are directed to the deepest parts of the respiratory tree because it markedly reduces the dosage in comparison with the oral route; it eliminates almost completely the systemic side effects; it allows the therapeutical action to be rapidly established.

The pressure aerosols, due to their ease of handling and to the feature that they allow the active ingredient to be rapidly and selectively administered, have met a great favour and are widely used both in the maintenance therapy of obstructive chronic respiratory diseases and in the treatment of acute fits of asthma.

Their apparent simplicity notwithstanding, the usual metered aerosols are difficult to use properly, and many reports from the scientific literature point out that the majority of patients employ the apparatus in an improper manner, either because they are not able to time the delivery in synchronism with breathing-in and do not inhale at the right time, or because they do not keep a suitable inspiration flow, or because they do not inhale deeply enough, or due to different reasons.

This problem is even more prominent with particular subjects, such as the children, elderly people and patients having reduced capabilities either from the point of view of respiration or from a manual point of view.

Even when the apparatus is used in the right manner, the availability of an inhaled drug to the air pathways depends in a large measure on the dimensions of the aerosol droplets, that in turn depend on the formulation and the evaporation time of the solvent. It is well supported by documentary evidence that even in the most favourable conditions only 10% of the dispensed dose of a metered aerosol reaches the air pathways: a similar percent is expired or deposited in the dispenser, while about 80%, due to the impact of high speed particles of aerosol, are deposited onto the mouth cavity and the pharynx, then being swallowed up and resorbed at a systemic level.

The inhaled portion of the drug, however, is usually enough to obtain the therapeutical effect.

Nevertheless, if the apparatus is not used in a proper way, the amount of drug reaching the action site at the lung level is further reduced and the therapeutical response is compromised. An excess deposition of active principle in the mouth-pharynx cavity can moreover give rise to undesirable effects both at systemic level as a consequence of the resorption of the drug and at a local level, such as it is the case with corticosteroids, that can give rise to mouth candidosis.

In a search to obviate the drawbacks that are connected with the use of metered aerosols, there have been developed in recent years expansion chambers.

These expansion chambers can be divided, according to their dimension features, in SPACERS and RESERVOIR BAGS or, more simply, RESERVOIRS.

The "spacers" are essentially expansion tubes that are inserted between the dispenser and the mouth for the purpose of increasing the proportion of drug that is deposited at a lung level, by acting on two factors: the dimension of the aerosol droplets and their impact in the mouth pharynx cavity.

The latency period between spray delivery and inhalation permits in fact a quick evaporation of the propellant with a reduction of the size of the particles before they enter the respiratory tree, thus helping them to better penetrate till the lower air pathways.

At the same time, the distance between dispenser and mouth thus obtained causes a slow-down of the particle speed, thus reducing the proportion of active principle that is lost due to the immediate impact against the walls of the oral cavity.

Finally a lower amount of propellants is inspired, with the consequence of a better compliance by the patient and a lower risk due to their possible toxicity.

The expansion chambers that are conventionally defined as spacers, share the features of a cylindrical shape and a rather low volume (70–100 ml).

Various spacer models are known:

simple devices that are in practice comparable with a cylindrical tube with mouth-piece, in which the dispenser is inserted in a perpendicular position (Fisons EP 89070, Huhtamaki WO 8502778); or in a parallel position (Newhouse EP 9667) relative to said tube;

apparatuses having a cylindrical shape as well in which the dispenser is in a transversal position relative to the spacer, said spacer being possibly telescopically extensible at the moment of use (Draco EP 15247 and EP 74937);

spacers comprising a first expansion chamber with a cylindrical shape, followed by a second one having a larger cross-section (Vortran Corp. PCT 2345/85, Hughes N. U.S. Pat. No. 4690332);

further similar models that simply have the advantage that they can be disassembled after use and employed as a container for the dispenser (American Cyanamid U.S. Pat. No. 3994421, U.S. Pat. No. 3897779, U.S. Pat. No. 3809294 and Rorer U.S. Pat. No. 4637528).

The use of this type of device has rapidly spread with the object of helping those patients who are not able to use in a proper way the usual metered aerosols or that meet difficulties in understanding their rather complex instructions.

The reports from the scientific literature do nevertheless agree that the application of small spacers does not produce appreciable improvements at a clinical level.

For this reasons, the research in this field has been addressed to providing large volume expansion chambers that are called "reservoirs".

The reservoirs, beside including the advantages of spacers, should also contribute in resolving the great problem of non-coordination between the dispensing maneuver and the inspiration because they permit the inspiration to be delayed of a few seconds relative to dispensing, thus helping also the patients having serious breathing difficulties.

The reservoirs share the characteristic of a great volume (about 700–1250 ml), while they exhibit various shapes, materials and construction characteristics. The main reservoir types that are described in literature are as follows:

rigid containers, with a round or pear-shape in which the usual spray can be inserted either in a position contiguous to the inhaling mouth-piece (Langaker K.E. SE 8200322) or in a diametrically opposite position (Draco SE 76012448);

bellows—like chambers, that should help the inspiration maneuver of the active principle, having the shape of collapsible bag (Key EP 50654) or of a cylindrical bag, flexible only along the side surface (Key EP 108145, Johns Hopkins Univ. EP 251443);

containers having a regular cylindrical shape, with a mouth-piece in a side position relative to the port for the connection to the can (Trutek U.S. Pat. No. 4534343), or in an opposite position;

devices that can be folded back after use and comprising a set of jointed telescopic beakers made of a transparent plastic material (Southampton Univ. GB 2110543), or a flexible bag provided within a rigid, telescopically retractible cylindrical container (Deshpaude GB 2182249).

The side and volume of these reservoirs are however such that in practice they are only limited to a domestic use.

We have now developed a new type of expansion chamber the size of which is comparable with that of spacers, but providing the effectiveness and manner of use of the reservoirs.

The object of the invention is to overcome the drawbacks of either apparatuses.

The device of the present invention comprises in fact the following features:

1) the volume of the chamber is 4–8 times greater than that of an usual spacer, with the consequence of a remarkable increase of the efficiency in slowing-down and evaporating the aerosol microdroplets;

2) it can be used as a reservoir by first dispensing and then inhaling the product, with no need of synchronising the two operations;

3) a one-way valve is provided at the mouth-piece, the function of said valve being both to prevent the aerosol spray that has been delivered into the chamber from exiting before the inhalation, and the patient from expiring into the apparatus;

4) the volume of the internal chamber can be adapted, thus allowing a diversified use according to the needs of the patients;

5) various kinds of dispensers can be inserted, whereby the apparatus can be used with different active substances;

6) the product can be housed inside the apparatus for an easier transportation;

7) its size is very limited, even though it has an appreciable volume of the expansion chamber, thereby making it easy to carry it even in limited spaces (pocket, bags, and so on), thereby overcoming the problem of a strictly domestic use;

8) as a consequence of the previous point, a higher effectiveness/dimensions ratio is achieved;

9) its use is very simple, thereby making it easily handled also by children.

The invention will now be described with reference to a merely illustrative, non-limiting embodiment thereof, said embodiment being illustrated in the enclosed drawing, in which:

FIG. 1 is a longitudinal section, in a diagrammatic representation, of the device according to the invention for dispensing metered aerosols to be inhaled; in the upper half of the figure, the internal tube is shown at the maximum extension position relative to the outer tube, while in the lower half the internal tube is in a completely receded position relative to the outer tube, corresponding to the stand-by condition of the apparatus;

FIG. 2 is a section along line A—A of FIG. 1;

FIG. 3 is a cross section of the mouth-piece of the apparatus for dispensing metered aerosols to be inserted into the rear opening of the internal tube;

FIG. 4 is a view of the mouth-piece of the reservoir in the direction of arrow B of FIG. 1.

The apparatus essentially comprises two coaxial tubes 1, 2, the internal tube 1 being slidable within the external tube 2 and separable. Said tubes delimit an internal chamber 3 the volume of which can be varied from about 200 ml to about 600 ml, depending on the degree of extension of the internal tube (1) relative to the outer one (2). The length of the chamber (3) may range from 100 to 300 mm and the maximum diameter from 50 to 80 mm.

The outer tube (2) (o.d.: 59.5 mm) has an open end 4, in which the internal tube can be inserted, while the opposite end 5 is tapered with a circular cross section (o.d.:33 mm). In end 5 four spokes 6 are provided in an orthogonal arrangement, said spokes stopping the four tabs 7 of a four-cuspid valve 8 against its opening towards the interior.

On the tapered end 5 (FIG. 2) the valve 8 is seated, whose characteristics are particularly important for the optimal operation of the apparatus as a whole.

Its purpose is to prevent both the leakage of the aerosol spray delivered into the chamber, before the inhalation, and the patient's expiration into the apparatus itself.

The cross section of the same configuration shown in FIG. 2 moreover allows, during inhalation, the aperture of a hole wide enough not to hinder the passage of the material to be inhaled also for a patient having respiratory difficulties.

Onto valve 8 the mouth-piece 9 of the reservoir is then assembled, the mouth-piece 9 having a final cross section like the final cross section of the dispensing mouth-piece 15 of the can (FIG. 3).

The internal tube 1 (o.d.: 51.5 mm) also includes an open end 10 that delimits the volume of the chamber, and an opposite end 11 provided with an opening 13 the cross section of which is slightly larger then that of the end opening 14 of the dispensing mouth-piece 15 (FIG. 3). Said opening 13 is also provided on the inner side with a set of lamellae (the number of said lamellae being four or six) that allow various kinds of mouth-pieces to be forced in.

The internal tube 1 slides within the outer tube 2, a polyethylene gasket 12 being provided between the two tubes, the gasket 12 being fixed outside at the open end 10. The gasket provides the seal of the apparatus against a leakage of the aerosol material and for the solidity of the assembly in the opened position.

Tubes 1, 2, as above-mentioned, can be separated; that is, the internal tube 1 can be completely removed from the outer tube 2. This feature has a double purpose: first it allows the spray can with mouth-piece to be housed inside the chamber 3, thus making it easier to be transported; secondly it permits a thorough cleaning of chamber 3.

The outer tube 2 carries two graphic symbols embossed on the outer surface: the first one, at the mouth-piece 9, shows the patient the end of the apparatus from which he should inhale; the second one is an arrow at the opposite end of tube 2 and on the same axis, directed towards the inner tube 1.

The inner tube, in turn, carries two arrows embossed on the outer surface and on the same axis spaced about 37 l mm from each other and directed towards the outer tube 2. Near the latter arrow the symbols 1 (near the proximal arrow relative to the bottom of the tube) and 2 (distal arrow), are embossed, said marks being provided to show the two extension positions recommended for use by children and adults, respectively.

An ideogram is finally embossed on the inner tube, at the bottom and coaxially relative to the above-mentioned arrows, said ideogram indicating the side of the apparatus in which the dispensing mouth piece 15 of the can is to be introduced.

The apparatus has a double function: first it causes the aerosol cloud delivered into the chamber to expand, thus slowing down the micro-droplets and enhancing the evaporation of the propellant therefrom, thereby reducing the average aerodynamic dimensions of the aerosol particles at the moment of inhalation and increasing the proportion of active substance having a size such as to allow it to reach the action site deep into the respiratory tree.

Secondly, the way of use of the apparatus, where the substance is first dispensed into chamber 3 and then inhaled from the opposite side through one-way valve 8 (that opens towards the patient at the moment of inspiration but not during expiration), allows it to be used by that remarkable proportion of patients having a chronic obstructive broncho-pulmonar illness who are not in a measure of properly using a normal MDI either because they cannot coordinate the delivery with the beginning of the respiratory act, or because they oppose an expiratory reflex upon the violent entry of the aerosol jet into the mouth.

The way of use of the device is very simple.

As already stated, the apparatus can be operated in connection with various types of metered aerosols.

Cap 15 is removed from the mouth-piece of the dispenser containing the prescribed product, then placing it onto the mouth-piece 9 of the expansion chamber 3. The internal tube 1 is then completely extracted and the product is housed into it; the internal tube is then completely inserted again into the outer tube 2. The assembly is now in a standby position, well closed, easily transportable even within a limited space.

At the moment of use, the assembly is removed from the bag, the cap is removed from mouth piece 9, the internal tube 1 is completely extracted and the mouth piece-carrying can is removed therefrom, the inner tube 1 is inserted again into the outer tube 2 until the opposite arrows on the two tubes are aligned (whereby two different positions can be selected by aligning the arrow on the outer tube with the first (position 1: children) or the second (position 2:adults) arrow of the inner tube, said position corresponding to a volume of chamber 3 of 290 ml or 380 ml, respectively).

The product carrying the mouth-piece is then inserted in an upside-down position into the bottom opening of the inner tube 1, pressing it until it is solidly blocked.

The mouth piece 9 of the receiver is, then taken between the lips, followed by completely expiring, dispensing the spray by pressing once on the bottom of the can and slowly breathing-in. The breath is held for at least 7 1 seconds before expiring again. Should it be necessary to administer a second dose, the above-mentioned procedure is repeated after allowing a time period of at least 30 seconds to elapse.

Finally, the dispensing mouth-piece 15 is removed from the reservoir, the reservoir is opened again by removing the internal tube 1, the mouth-piece-carrying can is introduced into it and the assembly is closed again. The cap is applied again to the mouth-piece 9 of the reservoir and the assembly is finally put away.

Comparison tests with metered aerosols of a conventional type, provided or not with the expansion chamber of the present invention, have proved that this device allows the amount of active substance that reaches the lower respiratory pathways, where it develops its therapeutical action, to be improved.

I claim:

1. A device for the administration of a drug to a patient in the form of a metered aerosol spray comprising an expansion chamber (3) consisting of an external tube (2) and an internal tube (1), the internal tube (1) being freely slidable within the external tube (2), said tubes delimiting said expansion chamber (3), the volume of which can be varied according to the amount of extension of said internal tube (1) relative to said external tube (2), said external tube (2) having an open end (4) for inserting the internal tube (1) and having a tapered end (5) opposite to said open end, a one-way valve (8) being housed in said tapered end, a first mouthpiece (9) open towards the patient being mounted on said valve, the internal tube (1) having an open end (10) that delimits the volume of said chamber (3) and having an opposite end (11), said end (11) having an opening (13), a second mouthpiece (15) of a conventional metered aerosol being placed in said opening, said tubes (1), (2) of said expansion chamber (3), said mouthpiece (9) and said opening (13) of said aerosol being on the same axis.

2. The device according to claim 1 wherein the volume of said expansion chamber (3) is varied between about 200 and 600 ml, the total length is varied between 100 and 300 mm and the maximum diameter is varied between 50 and 80 mm.

3. The device according to claim 1 wherein said one way valve (8) prevents the aerosol spray delivered into said chamber from exiting before the inhalation, and prevents air from being expired into the apparatus.

4. The device according to claim 1, wherein said tubes (1), (2) are completely separable.

5. The device according to claim 1 wherein said metered aerosol has a can, said can is housed inside said internal tube (1) and said internal tube (1) is fixed into said external tube (2) for storage and transportation assembly.

6. The device according to claim 1 wherein said tapered end (5) has a circular cross section.

7. The device according to claim 1 wherein four spokes (6) are placed on said tapered end (5).

8. The device according to claim 1 wherein said first mouthpiece of said expansion chamber (9) and said second mouthpiece of said metered aerosol have the same cross section.

9. The device according to claim 1 wherein said one-way valve has tabs (7).

* * * * *